(12) United States Patent
Nobis et al.

(10) Patent No.: US 7,850,686 B2
(45) Date of Patent: Dec. 14, 2010

(54) PROTECTIVE NEEDLE KNIFE

(75) Inventors: Rudolph H. Nobis, Mason, OH (US); Kurt Bally, Lebanon, OH (US); Christopher Paul Swain, London (GB)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 667 days.

(21) Appl. No.: 11/277,998

(22) Filed: Mar. 30, 2006

(65) Prior Publication Data

US 2007/0250057 A1 Oct. 25, 2007

(51) Int. Cl.
*A61B 18/18* (2006.01)
(52) U.S. Cl. .......................................... 606/45; 606/41
(58) Field of Classification Search ................ 606/34, 606/37, 39–42, 45, 167, 171–172; 604/164.01, 604/164.06, 164.08
See application file for complete search history.

(56) References Cited

U.S. PATENT DOCUMENTS

| 3,595,239 | A | | 7/1971 | Petersen |
| 4,535,773 | A | | 8/1985 | Yoon |
| 4,601,710 | A | * | 7/1986 | Moll ..................... 604/164.12 |
| 4,654,030 | A | | 3/1987 | Moll et al. |
| 5,281,218 | A | | 1/1994 | Imran |
| 5,380,321 | A | * | 1/1995 | Yoon ........................... 606/41 |
| 5,599,347 | A | * | 2/1997 | Hart et al. ..................... 606/42 |
| 5,797,906 | A | | 8/1998 | Rhum et al. |
| 5,807,395 | A | * | 9/1998 | Mulier et al. ................. 606/41 |
| 6,156,006 | A | | 12/2000 | Brosens |
| 6,193,717 | B1 | * | 2/2001 | Ouchi .......................... 606/49 |
| 6,293,952 | B1 | * | 9/2001 | Brosens et al. .............. 606/119 |
| 6,743,206 | B1 | | 6/2004 | Smith et al. |
| 2002/0111620 | A1 | * | 8/2002 | Cooper et al. ................. 606/41 |
| 2003/0032924 | A1 | | 2/2003 | Scarfone et al. |
| 2005/0228286 | A1 | | 10/2005 | Messerly et al. |
| 2006/0253183 | A1 | * | 11/2006 | Thagalingam et al. ....... 607/120 |
| 2007/0135803 | A1 | * | 6/2007 | Belson .......................... 606/1 |
| 2007/0191830 | A1 | * | 8/2007 | Crompton et al. ............. 606/41 |

FOREIGN PATENT DOCUMENTS

| DE | 19847852 | 4/1999 |
| WO | WO-00/18307 | 4/2000 |

* cited by examiner

*Primary Examiner*—Thomas J Sweet
*Assistant Examiner*—Amanda Scott
(74) *Attorney, Agent, or Firm*—Nutter McClennen & Fish LLP (57) ABSTRACT

Various methods and devices are provided for penetrating tissue. In one embodiment, a tissue-penetrating device is provided and includes a flexible elongate shaft and a flexible elongate wire extending through the elongate shaft and having a needle tip at a distal end thereof for penetrating tissue. The needle tip can be conductive and the elongate wire can be adapted to couple to an energy source for delivering energy to the needle tip to facilitate penetration of the needle tip through tissue. The device can also include a protective sheath disposed over at least a portion of the elongate shaft and movable relative to the elongate shaft between a distal position and a proximal position. The protective sheath is configured to either protect the needle tip or electrically isolate the needle tip after the needle tip is penetrated through tissue, thereby preventing unintentional penetration of adjacent tissue.

22 Claims, 7 Drawing Sheets

PROTECTIVE NEEDLE KNIFE

FIELD OF THE INVENTION

The present invention relates to methods and devices for penetrating tissue, and in particular to a needle knife having a safety feature.

BACKGROUND

Laparoscopic surgery is one type of minimally invasive surgery in which a surgeon uses numerous trocar ports to access and visualize the tissue site of interest within the abdominal cavity of a fully anesthetized patient. The benefits of laparoscopic surgery, as compared to open incisional, abdominal surgery, include less pain, shorter recovery time, less scarring, and lower cost. Another way to access the abdominal cavity, however, is via natural openings (mouth, anus, vagina, urethra) of the body and through the peritoneal lining of the abdominal cavity. Obviously, the size and shape of instruments that may be passed through a body lumen in order to perform a medical procedure in the abdominal cavity are greatly restricted due to the anatomical properties of the lumen.

General surgeons, gastroenterologists, and other medical specialists routinely use flexible endoscopes for intraluminal (within the lumen of the alimentary canal) examination and treatment of the upper gastrointestinal (GI) tract, via the mouth, and the lower GI tract, via the anus. In these procedures, the physician pushes the flexible endoscope into the lumen, periodically pausing to articulate the distal end of the endoscope using external control knobs, to redirect the distal tip of the endoscope. In this way, the physician may navigate the crooked passageway of the upper GI past the pharynx, through the esophagus and gastro esophageal junction, and into the stomach. The physician must take great care not to injure the delicate mucosal lining of the lumen, which generally may stretch open to a diameter in the range of about 15-25 mm, but normally has a non-circular cross sectional configuration when relaxed.

During such translumenal procedures, a puncture must be formed in the stomach wall or in the gastrointestinal tract to access the peritoneal cavity. One device often used to form such a puncture is a needle knife which is inserted through the working channel of the endoscope, and which utilizes energy to penetrate through the tissue. A guidewire is then feed through the endoscope and is passed through the puncture in the stomach wall and into the peritoneal cavity. The needle knife is removed, leaving the guidewire as a placeholder. A balloon catheter is then passed over the guidewire and through the working channel of the endoscope to position the balloon within the opening in the stomach wall. The balloon can then be inflated to increase the size of the opening, thereby enabling the endoscope to push against the rear of the balloon and to be feed through the opening and into the peritoneal cavity. Once the endoscope is positioned within the peritoneal cavity, numerous procedures can be performed through the working channel of the endoscope.

While the current methods and devices used to penetrate tissue are effective, one drawback is the risk of damaging adjacent organs and tissue. Due to the low amount of energy and force of penetration needed to pass through tissue, there is the risk of penetrating adjacent tissue that is intended to be left unharmed during the procedure. Accordingly, there remains a need for improved tissue penetrating devices that include a safety feature to protect adjacent tissue. There also remains a need for a simplified procedure that requires less steps to form a puncture in tissue.

SUMMARY

The present invention provides devices and methods for endoscopically or laparoscopically penetrating tissue. In one exemplary embodiment, a tissue-penetrating device is provided and includes a flexible elongate shaft and a flexible elongate wire extending through the elongate shaft and having a needle tip at a distal end thereof for penetrating tissue. The needle tip can be conductive and the elongate wire can be adapted to couple to an energy source for delivering energy to the needle tip to facilitate penetration of the needle tip through tissue The device can also include a protective sheath disposed over at least a portion of the elongate shaft and movable relative to the elongate shaft between a distal position and a proximal position. The protective sheath is configured to protect the needle tip or electrically isolate the needle tip after the needle tip is inserted through tissue, thereby preventing unintentional penetration of adjacent tissue.

In one exemplary embodiment, the needle tip can be separable from the elongate wire and it can be attached to the protective sheath. The needle tip can be spaced apart from a distal end of the elongate wire when the protective sheath is in the distal position, and the protective sheath can move the needle tip into contact with the elongate wire when the protective sheath moves to the proximal position to allow energy to be delivered from the elongate wire to the needle tip. In an exemplary embodiment, the protective sheath is adapted to move from the distal position to the proximal position when the protective sheath is advanced into a tissue surface. The device can further include a biasing element disposed between the protective sheath and the elongate shaft for biasing the protective sheath to the distal position. The biasing element can be disposed within the protective sheath and around a portion of the elongate shaft. The elongate shaft can include an abutment configured to receive a force applied to the biasing element by movement of the protective sheath.

In another exemplary embodiment, the needle tip can be formed on the distal end of the elongate wire, and it can be positioned proximal to a distal-most end of the protective sheath when the sheath is in the distal position, and it can be exposed and extend from the protective sheath when the protective sheath is in the proximal position. The protective sheath can be adapted to move from the distal position to the proximal position when the protective sheath is advanced into a tissue surface. A biasing element can be disposed between the protective sheath and the elongate shaft for biasing the protective sheath to the distal position, and it can be disposed within the protective sheath and around a portion of the elongate shaft. The elongate shaft can include an abutment configured to receive a force applied to the biasing element by movement of the protective sheath.

In another embodiment, the device can include an expandable member disposed around a portion of the elongate shaft and adapted to expand radially relative to the elongate shaft. In one embodiment, the expandable member can be an expandable balloon. The device can also include various other features. For example, the needle tip can be configured to form a puncture hole in tissue that has an extent that is substantially equal to a diameter of the protective sheath to allow the protective sheath to pass through the puncture hole.

Also disclosed herein are methods for penetrating tissue. In one embodiment, the method can include inserting a flexible elongate shaft through a body lumen, e.g., translumenally, and positioning a distal tip of the elongate shaft adjacent to a tissue surface to be penetrated. Force can be applied to the elongate shaft to cause a protective sheath disposed around a distal end of the elongate shaft to move proximally to allow a needle tip extending from a distal end of the protective sheath to penetrate through the tissue. Energy can be delivered to the needle tip through an elongate wire disposed in the elongate shaft. In one embodiment, the needle tip can be mated to the protective sheath and it can be electrically isolated from the elongate wire when the protective sheath is in a distal position, and movement of the protective sheath proximally can be effective to position the needle tip in contact with the elongate wire.

In another embodiment, the needle tip can be positioned proximal to a distal-most end of the protective sheath when the protective sheath is in a distal position, and movement of the protective sheath proximally can be effective to expose the needle tip to allow the needle tip to penetrate through tissue. The protective sheath can return to the distal position once the needle tip penetrates through the tissue.

In a further embodiment, an expandable member disposed on the elongate shaft can be expanded to increase a size of a puncture hole formed by the needle tip after the needle tip penetrates through the tissue. The expandable member can be inflated with air or fluid. In another embodiment, the needle tip can be removed by pulling on an elongate wire coupled to the needle tip, and a guidewire can be inserted through the flexible elongate shaft to position the guidewire through the puncture formed in the tissue by the needle tip. In yet another embodiment, the needle tip can form a puncture hole in the tissue having an extent that is substantially equal to a maximum diameter of the protective sheath to facilitate insertion of the protective sheath through the puncture hole formed in the tissue.

BRIEF DESCRIPTION OF THE DRAWINGS

The invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary methods and devices are provided for penetrating tissue. In particular, a device is provided having a flexible elongate wire extending through an elongate shaft and having a needle tip at a distal end thereof for penetrating tissue. The device can also include a protective sheath disposed over at least a portion of the elongate shaft and configured to allow the needle tip to penetrate tissue only when the protective sheath is advanced into the tissue to be penetrated. While the device can be used in a variety of applications, it is preferably used in endoscopic or laparoscopic surgery. For example, the device can be inserted translumenally, and then penetrated through a tissue surface, such as the stomach, to form a puncture hole in the tissue to provide access to other areas of the body, such as the abdominal cavity. The protective sheath is particularly advantageous as it allows the device to penetrate through tissue, while preventing puncture or injury to adjacent tissue, such as organs disposed within the stomach cavity.

Figure 1A:
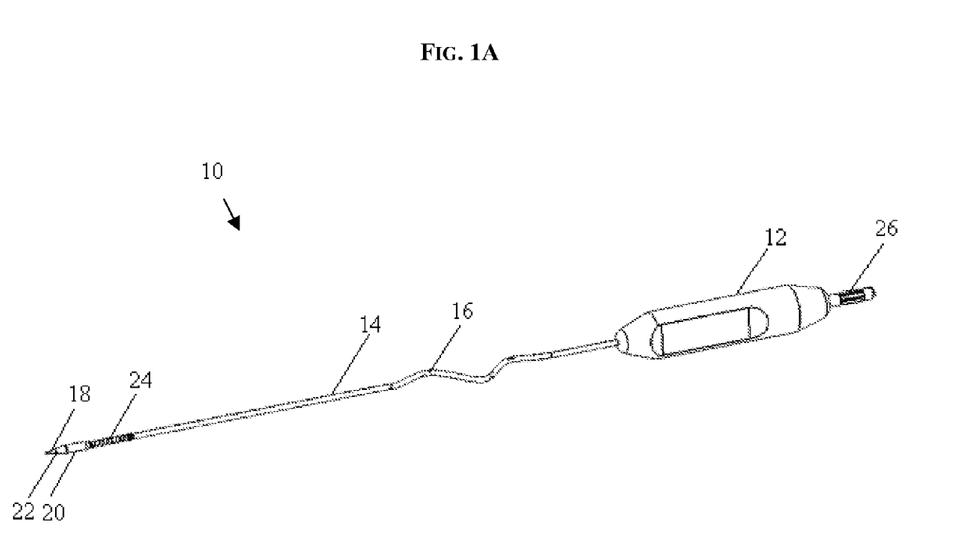
FIG. 1A is a perspective view of one exemplary embodiment of a device for penetrating tissue.

FIG. 1A illustrates one exemplary embodiment of a device for penetrating tissue. As shown, the device 10 generally includes a handle 12 with a flexible elongate shaft 14 extending therefrom and configured to be introduced translumenally. The elongate shaft 14 includes a flexible elongate wire 16 extending from the handle 12 through a hollow channel (not shown) in the shaft 14. A needle tip 18 is formed on or coupled to a distal end of the elongate wire 16 for penetrating tissue. The device 10 also includes a protective sheath 20 disposed over a distal end of the shaft 14 and configured to protect the needle tip 18 until it is positioned adjacent to tissue to be penetrated, as will be discussed in more detail below. The device 10 is also preferably adapted to coupled to an energy source to allow the needle tip 18 to be energized to facilitate penetration through tissue.

The handle 12 of the device 10 can have any shape and size but it is preferably adapted to facilitate grasping and manipulation of the device. As shown in FIG. 1A, the handle 12 has a generally elongate cylindrical configuration. The handle 12 can also include other features, such as an actuating element (not shown) to enable the delivery of energy from an energy source through the elongate wire 16 to the needle tip 18, as will be discussed below. By way of non-limiting example, the actuating element can be a button, a switch, a knob, or any other member configured to actuate delivery of energy from an energy source. In lieu of an actuating element disposed on the handle 12, one skilled in the art will appreciate that the actuating element can be located elsewhere, including on a foot pedal. The energy source can be an internal energy source, such as a battery disposed in the handle 12, or the handle 12 can be adapted to be coupled to an external energy source. For example, a wire 26, a portion of which is shown in FIG. 1A, can include a plug on a terminal end thereof for coupling the handle 12 to a power outlet.

The shaft 14 of the device can also have a variety of configurations, and it can be flexible or rigid depending on the intended use. As noted above, the shaft 14 is preferably adapted to be inserted translumenally, and therefore at least portions of the shaft 14 are preferably semi-flexible or flexible to allow insertion through a tortuous lumen. One skilled in the art will appreciate that the shaft 14 can be made from a variety of biocompatible materials that have properties sufficient to enable the shaft 14 to be inserted and moved within channels of a body lumen. The shaft 14 can also have an elongate length to allow the distal end of the shaft 14 to be positioned within the body while the proximal end remains external to the body. While the length can vary, in an exemplary embodiment, the length is in the range of about 100 mm to 300 mm. The shaft 14 can also include one or more inner lumens extending therethrough for receiving the elongate wire 16. The inner lumen(s) of the shaft 14 can also be used to pass other instruments or fluids through the device for use during a surgical procedure.

The elongate wire 16 that extends through the shaft 14 can also have a variety of configurations, and it can be flexible or rigid depending on the intended use. In an exemplary embodiment, the elongate wire 16 is adapted to be used translumenally, and therefore is semi-flexible or flexible to allow it to bend and flex with the shaft 14 through a tortuous lumen. The elongate wire 16 is also preferably adapted to deliver energy to a needle tip 18 formed on or coupled to the distal end of the elongate wire 16 to facilitate penetration of the needle tip 18 through tissue. One skilled in the art will appreciate that the elongate wire 16 can be made from a variety of conductive materials that have properties sufficient to enable the elongate wire 16 to conduct and deliver energy to tissue through the needle tip 18. In one embodiment, the elongate wire 16 can be a single wire electrode. The elongate wire 16 can also include other features, such as an inner lumen extending therethrough for receiving fluid, such as saline or water. The fluid can be used to irrigate the tissue site during penetration by the needle tip 18. While the elongate wire 16 can have a variety of lengths, it preferably is of a fixed length extending from the handle 12 to a position proximal to a distal-most end of the protective sheath 20. This prevents the elongate wire 16 from extending beyond the protective sheath 20 when the protective sheath 20 is in the distal position and the device 10 is not in contact with tissue.

The needle tip 16 can have various shapes and sizes as well. In one embodiment, illustrated in FIG. 1B, the needle tip 18 generally has a blunt distal end that can penetrate through tissue only when energy is delivered thereto. The proximal end of the needle tip 18 is integrally formed with or coupled to the distal end of the elongate wire 16 to establish an electrical connection with an energy source. The needle tip 18 can also be made from a variety of materials. For example, while the needle tip 18 is adapted to be conductive, it need not be made entirely of conductive material as long as a conductive path exists through the needle tip 18. If made from entirely conductive materials, a portion of the needle tip 18 can be coated with an insulating material. In other embodiments, the needle tip 18 can be made from a composite material, which includes conductive and non-conductive materials.

One skilled in the art will appreciate that the needle tip can have a variety of other configurations and it can be adapted to treat tissue in a variety of ways. For example, the needle tip can penetrate tissue, such as by cutting the tissue. The needle tip can be blunt and tissue penetration can be effected or assisted by electrical energy, and/or it can be sharpened so that it penetrates tissue by mechanical action. Where the needle tip 18 uses energy, i.e., electrosurgical cutting to penetrate tissue, a sufficient voltage will create an electric spark between the needle tip 18 and the tissue. When the arcing occurs, the cellular fluid gets superheated, for example, to a temperature greater than 600 degrees Celsius, and the cells swell up due to the internal steam pressure within the cell. This can cause the cells to explode and vaporize, thus allowing the needle tip 18 to penetrate the tissue. Other exemplary configurations of a needle tip are also disclosed herein and can be used with the device of FIGS. 1A and 1B.

Figure 1B:
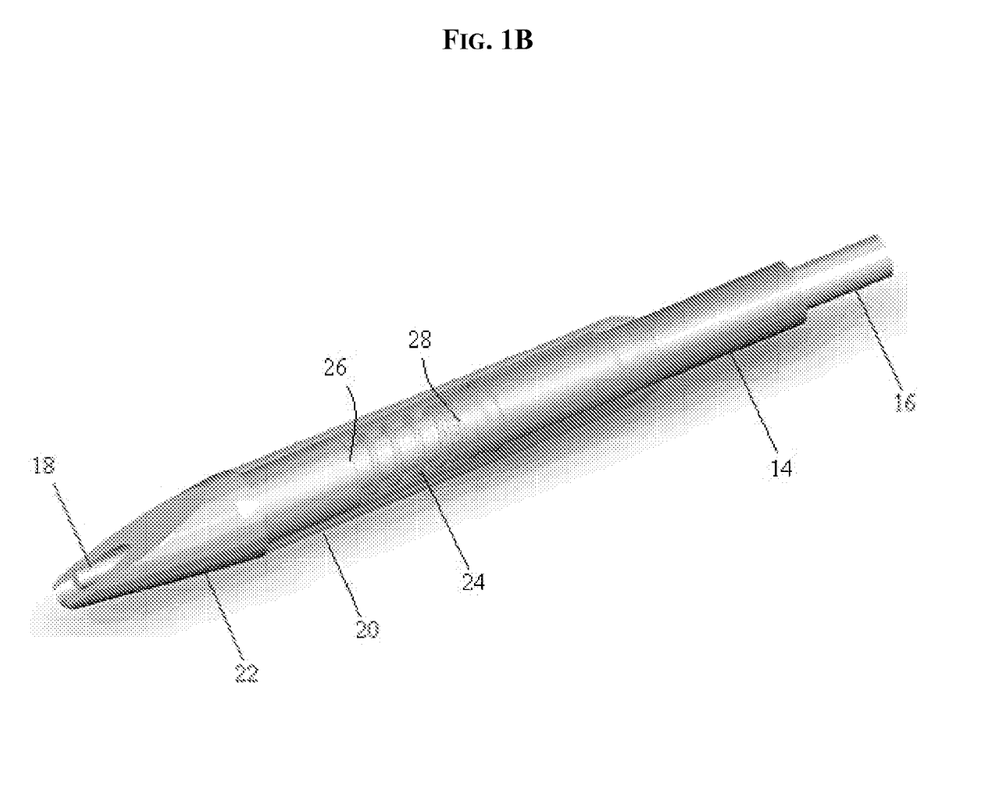
FIG. 1B is a partially transparent perspective view of a distal portion of the device shown in FIG. 1A.

The protective sheath 20 can also have various shapes and sizes, but in the illustrated embodiment, it has a generally hollow configuration with a tapered conical tip having an opening through which the needle tip 18 can pass. As shown in FIG. 1B, the tip of the protective sheath 20 can be in the form of an end cap 22 that is fixedly attached to the tubular protective sheath 20, or the end cap 22 can be integrally formed with the protective sheath 20. The protective sheath 20 and the end cap 22 can be mated using a variety of techniques, including male and female connectors that enable temporary or permanent attachment between the protective sheath 20 and the end cap 22, or a variety of other methods such as adhesive bonding, that enable the end cap 22 to be mounted to the protective sheath 20. In use, shown in FIG. 1B, the protective sheath 20 is disposed over at least a portion of the shaft 14 and the needle tip 18, and it can be configured to move between a distal position, in which the needle tip 18 is substantially disposed within the protective sheath 20, and a proximal position, in which the needle tip 18 extends distally from the protective sheath 20.

As noted above, the protective sheath 20 is moveable between a distal and proximal position. In its distal position, as shown in FIG. 1B, the needle tip 18 does not extend past the distal-most end of the protective sheath 20, preventing the needle tip 18 from penetrating tissue. The needle tip 18 can be fully contained within the protective sheath 20, or it can be disposed within the opening in the tip, as shown. The force of the distal end of the protective sheath 20 against a tissue to be treated causes the protective sheath 20 to move in a proximal direction over the shaft 14. When so positioned, the needle tip 18 extends past the distal-most end of the protective sheath 20 to allow the needle tip 18 to contact and penetrate the tissue. After the needle tip 18 has penetrated the target tissue, or the device 10 has been moved out of contact with the target tissue, the pressure is removed from the protective sheath 20, thereby allowing the protective sheath 20 to move distally to cover the distal end of the needle tip 18 to prevent continued tissue penetration.

In an exemplary embodiment, the device 10 can include a biasing element that is adapted to bias the protective sheath 20 to the distal position. In one embodiment, the biasing element can be a spring 24, as shown in FIG. 1B, for biasing the protective sheath 20 to the distal position. The spring 24 can be disposed around the shaft 14 with its distal end resting against a distal abutment 26 formed within the protective sheath 20 and its proximal end resting against a proximal abutment 28 formed on the shaft 14. The biasing force of the spring 24 on the protective sheath 20 can be overcome by advancing the protective sheath 20 against a tissue surface, allowing the protective sheath 20 to retract into the proximal position when it is in contact with a tissue. As the protective sheath 20 moves proximally, the spring 24 compresses and the needle tip 18 is exposed to allow it to contact the tissue. A person skilled in the art will appreciate that a variety of other biasing elements can be used to bias the protective sheath 20 to a distal position.

Figure 2:
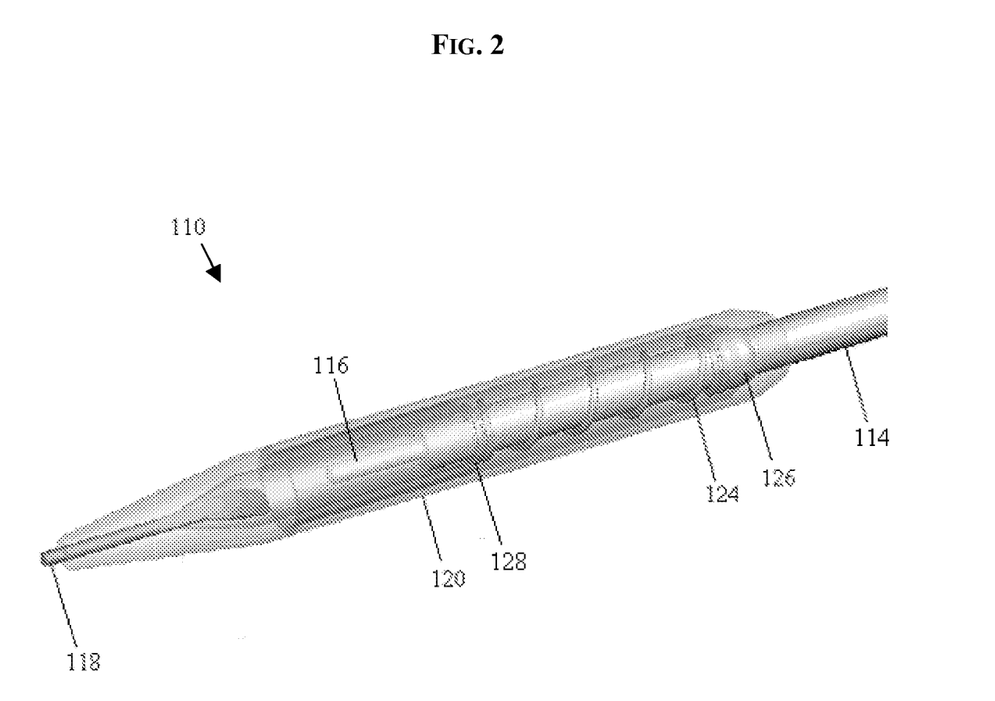
FIG. 2 is a partially transparent perspective view of a distal portion of another embodiment of a device for penetrating tissue.

In other embodiments, rather than the protective sheath 20 moving proximally to expose the needle tip 18 as described above, the needle tip and the protective sheath can move together to electrically couple the proximal end of the needle tip with a distal end of the elongate wire. This is illustrated in FIG. 2, which shows a device 110 having a protective sheath 120 disposed over at least a portion of the distal end of an elongate shaft 114. An elongate wire 116 extends through or is integrally formed with the elongate shaft 114, and a needle tip 118 is separable from the elongate wire 116 and it is fixedly coupled to the protective sheath 120. The protective sheath 120 includes an opening at its distal end through which the distal end of the needle tip 118 extends.

In use, the protective sheath 120 is movable between a distal position and a proximal position, in a manner similar to that previously described with respect to FIG. 1B. The needle tip 118 is spaced apart from the distal end of the elongate wire 116 when the protective sheath 120 is in a distal, deactivated position. When a distal end of the needle tip 118 contacts tissue, the force of the tissue on the distal end of the needle tip 118 can move the protective sheath 120 and the needle tip 118 in a proximal direction, such that the needle tip 118 comes into contact with the distal end of the elongate wire 116 to allow energy to be delivered from the energy source through the elongate wire 116 to the needle tip 118.

The device 110 can also include a biasing element that is adapted to bias the protective sheath 120 and the needle tip 118 to one of the deactivated or activated positions. By way of example, the biasing element can be a spring 124, similar to spring 24 as described above in relation to FIG. 1B. In the embodiment shown in FIG. 2, the spring 124 is disposed around the elongate shaft 114 with its proximal end resting against a proximal abutment 126 disposed on the elongate shaft 114, and its distal end resting against a distal abutment 128 formed within the protective sheath 120. The biasing force of the spring 124 on the protective sheath 120 and the needle tip 118 can be overcome by advancing the protective sheath 120 against a tissue surface, allowing the protective sheath 120 and the needle tip 118 to retract into the proximal activated position. As the protective sheath 120 and the needle tip 118 move proximally, an electrical connection is established between the needle tip 118 and the elongate wire 116, allowing energy to be delivered to the needle tip 118 through the elongate wire 116 from the energy source to allow the needle tip 118 to penetrate tissue. Once the tissue penetration has occurred, the force on the needle tip 118 and the protective sheath 120 is removed, allowing them to move distally to the deactivated position. A person skilled in the art will appreciate that a variety of other devices, or configurations, suitable for biasing can be used as the biasing element.

In another exemplary embodiment, the tissue-penetrating devices disclosed herein can be configured to receive a guidewire therethrough for guiding additional devices through the puncture created in the penetrated tissue. By way of non-limiting example, the elongate wire 16 and the needle tip 18 of the device of FIGS. 1A-1B can be removed from the device 10 by pulling on a proximal end of the elongate wire 16. A guidewire (not shown) can be inserted into the shaft 14 to position the guidewire through the puncture formed in the tissue by the needle tip 18. Once the guidewire has been positioned through the shaft 14, the shaft 14 can be removed, leaving the guidewire in place. A variety of devices and surgical instruments can then be guided along the guidewire to facilitate a number of surgical procedures that can be performed at the site of the penetrated tissue.

Figure 4A:
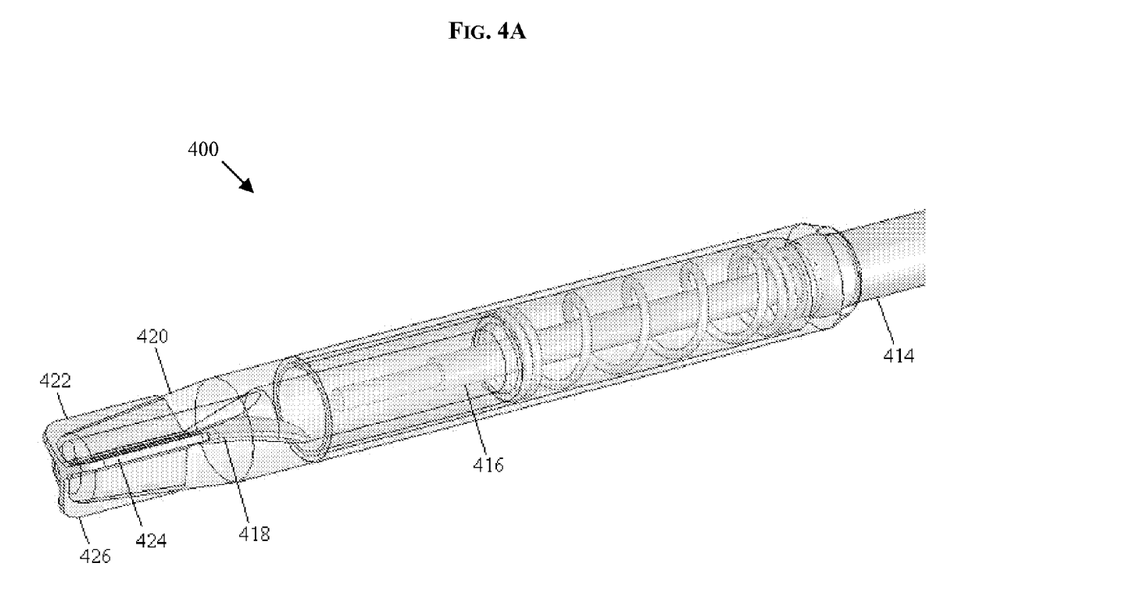
FIG. 4A is a partially transparent perspective view of a distal portion of another embodiment of a device having a needle tip with a multi-bladed configuration.
Figure 4B:
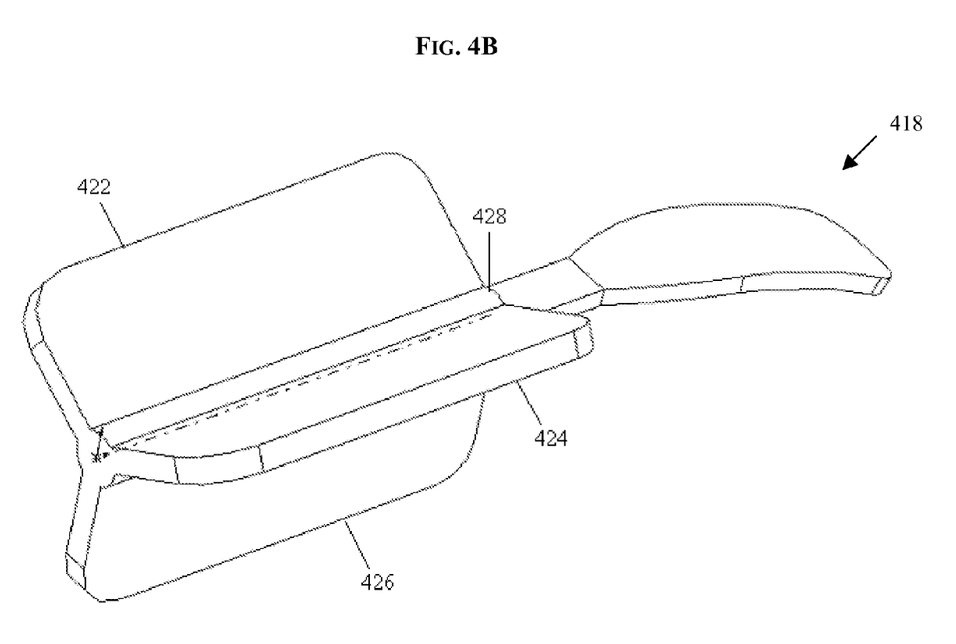
FIG. 4B is a perspective view of the needle tip shown in FIG. 4A.

As previously mentioned, the needle tip of the tissue-penetrating device can have a variety of other configurations. For example, the needle tip can have a maximum width that is substantially equal to a maximum width of the protective sheath, thereby facilitating insertion of the protective sheath through tissue. In other words, the needle tip can be configured to form a penetration or cut in tissue that has an extent, e.g., a diameter or width, that is substantially equal to a diameter of the sheath. While various techniques can be used to form such a needle tip, FIGS. 4A-4B illustrate one such exemplary embodiment. In this embodiment, a device 400 is similar to the device of FIG. 2, except that a needle tip 418 has a multi-bladed configuration, at least at its distal-most end. In particular, the needle tip 418 includes three planar members 422, 424, 426 that extend radially outward from a central shaft 428, and that are spaced substantially equidistant apart form one another around the shaft 428, as best shown in FIG. 4B. In order to accommodate the needle tip 418, a protective sheath 420 of the device 400 can likewise include three corresponding slits formed therein for receiving the planar members 422, 424, 426, as illustrated in FIG. 4A. In use, the needle tip 418 will form a cut in the tissue, and the extent or diameter of the cut will be substantially equal to the diameter of the protective sheath 420, thereby allowing the protective sheath 420 to be inserted through the tissue.

Figure 4C:
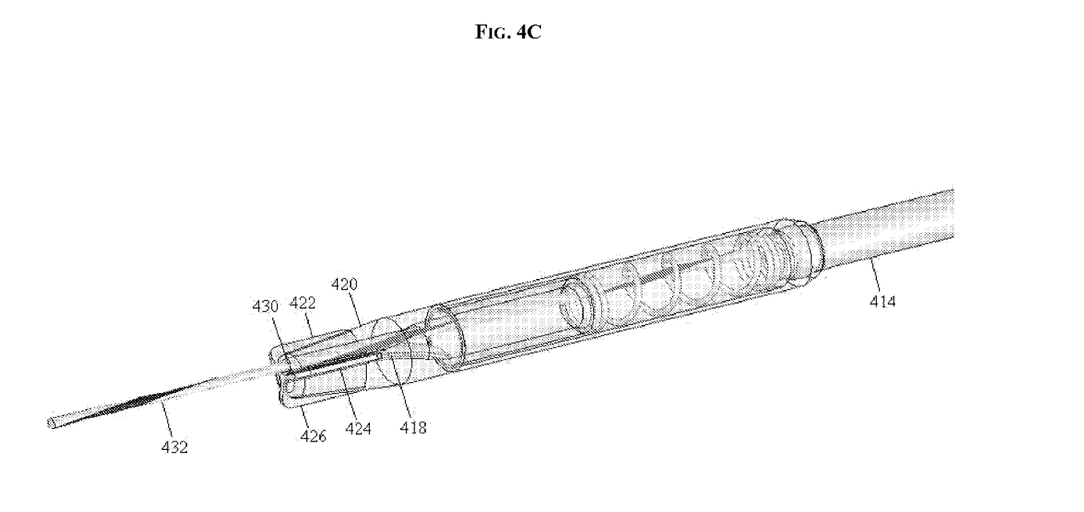
FIG. 4C is a partially transparent perspective view of the device shown in FIG. 4A having a guidewire inserted through the device.

The device of FIG. 4A can also be configured to receive a guidewire therethrough. As shown in FIG. 4C, the distal-most end of the protective sheath 420 can include a guidewire port 430 formed therein that is positioned offset from the slits for receiving the needle tip 418. Thus, a guidewire 432 can extend substantially adjacent to an elongate wire 416 through a shaft 414, and it can extend out of the guidewire port 430 to be positioned through the tissue.

Figure 3:
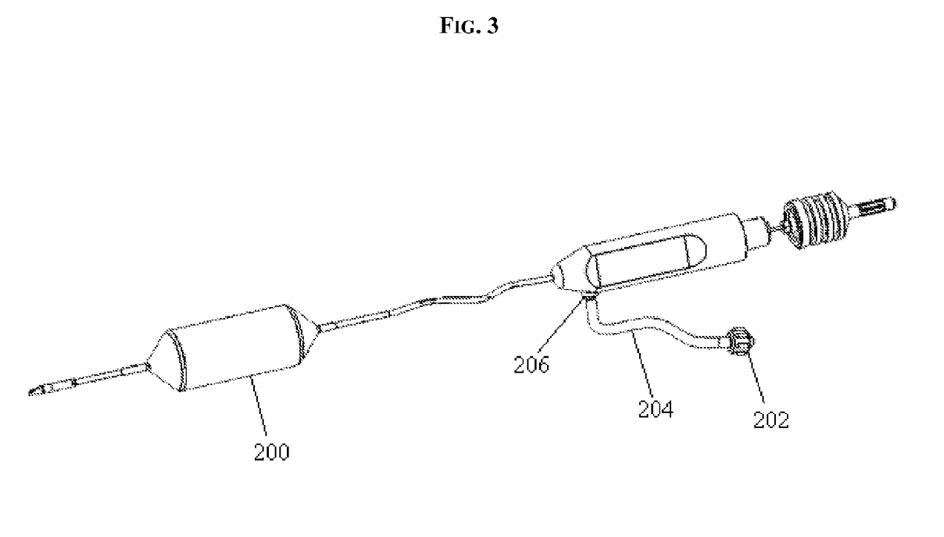
FIG. 3 is a perspective view of another embodiment of a device for penetrating tissue having an expandable member for increasing the size of a puncture formed in tissue using the device.

The various devices disclosed herein can also include an expandable member that is adapted to increase the size of the puncture formed in tissue by a needle tip. FIG. 3 illustrates one embodiment of an expandable member disposed on the device 10 of FIGS. 1A-1B. As shown, the expandable member is in the form of a dilating balloon 200 that is configured to be inflated to expand the size of the puncture. A person skilled in the art will appreciate that a variety of other expandable members can be used to expand a puncture created by a needle tip. When used in conjunction with the embodiment illustrated in FIGS. 1A-1B, the balloon 200 can be disposed on the elongate shaft 14 at a location proximal to the protective sheath 20. After the needle tip 18 and the protective sheath 20 have penetrated through tissue, the device 10 can be advanced to position the deflated balloon 200 within the puncture site. The balloon 200 can then be inflated using, for example, fluid or air introduced through a lumen in the device. As shown in FIG. 3, the device can include an insufflation tube 204 having a proximal port 202 and a distal connector 206 coupled to the handle. In other embodiments, a port can be formed directly in the handle. A person skilled in the art will appreciate that the expandable member can be associated with other devices, such as the guidewire described above. For example, the expandable member can be disposed on or positioned over the guidewire to allow for positioning the expandable member within the puncture site.

The tissue-penetrating devices described herein can also be used with other surgical device or instruments. For example, an endoscope can be passed through the esophagus and positioned within the stomach. A tissue-penetrating device, such as the devices 10, 110 described in FIGS. 1A-2, can be introduced through a working channel of the endoscope and used to create a puncture hole in the stomach wall by penetrating the tissue of the stomach wall. A guidewire can then be feed through the device to the site of the puncture hole created in the stomach wall, and the tissue-penetrating device can be removed, leaving the guidewire as a placeholder. An expandable member disposed on the guidewire or positioned over the guidewire can be positioned within the puncture site. Once the expandable member has been inflated and the size of the puncture hole in the stomach wall has been increased, the endoscope can be advanced into the expandable member to push the expandable member and the endoscope through the puncture hole and into the abdominal cavity. A person skilled in the art will appreciate that a guidewire and separate expandable member are not necessary where the tissue-penetrating devices include an expandable member. In such a case, the expandable member can be positioned within the puncture and expanded to enlarge the puncture. The endoscope can then be advanced into the expandable member to push the expandable member and thus the endoscope through the puncture. Additional instruments and devices can then be passed through the working channel of the endoscope to perform various procedures.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for penetrating tissue, comprising:
   inserting a flexible elongate shaft through a body lumen;
   positioning a distal tip of an elongate wire extending through the elongate shaft adjacent to a tissue surface to be penetrated, and;
   applying force to a distal end of the elongate shaft to cause a protective sheath disposed around a distal end of the elongate wire and around a distal end of the elongate shaft to move proximally by overcoming a biasing force of a biasing element disposed within the protective sheath and around a distal end of the elongate shaft to allow a needle tip extending from a distal end of the protective sheath to penetrate through the tissue.

2. The method of claim 1, further comprising delivering energy through the elongate wire disposed in the elongate shaft to the needle tip.

3. The method of claim 2, wherein the needle tip is mated to the protective sheath and is electrically isolated from the elongate wire when the protective sheath is in a distal position, and wherein movement of the protective sheath proximally is effective to position the needle tip in contact with the elongate wire.

4. The method of claim 1, wherein the needle tip is positioned proximal to a distal-most end of the protective sheath when the protective sheath is in a distal position, and wherein movement of the protective sheath proximally is effective to expose the needle tip to allow the needle tip to penetrate through tissue.

5. The method of claim 1, wherein the protective sheath returns to a distal position once the needle tip penetrates through tissue.

6. The method of claim 1, further comprising, after the needle tip penetrates through the tissue, positioning an expandable member disposed on the elongate shaft within a puncture hole formed in the tissue by the needle tip, and expanding the expandable member to increase a size of the puncture hole.

7. The method of claim 6, wherein the expandable member is inflated with fluid.

8. The method of claim 1, further comprising removing the needle tip by pulling on an elongate wire coupled to the needle tip, and inserting a guidewire through the flexible elongate shaft to position the guidewire through a puncture hole formed in the tissue by the needle tip.

9. The method of claim 1, wherein the elongate shaft is inserted into a body lumen translumenally.

10. The method of claim 1, wherein the tissue being penetrated is the stomach wall.

11. The method of claim 1, wherein the needle tip forms a puncture hole in the tissue having an extent that is substantially equal to a maximum diameter of the protective sheath to facilitate insertion of the protective sheath through the puncture hole formed in the tissue.

12. A tissue-penetrating device, comprising:
    a flexible elongate shaft;
    a flexible elongate wire extending through the elongate shaft and having a needle tip at a distal end thereof for penetrating tissue;
    a protective sheath disposed over a distal end of the elongate shaft and a distal end of the elongate wire and movable relative to the elongate shaft between a distal position and a proximal position; and
    a biasing element disposed within the protective sheath and around the distal end of the elongate shaft, the biasing element having a distal end that rests against a distal abutment formed within the protective sheath and a proximal end that rests against a proximal abutment formed on the elongate shaft, the biasing element configured to bias the protective sheath to the distal position.

13. The device of claim 12, wherein the needle tip is conductive and the elongate wire is adapted to couple to an energy source for delivering energy to the needle tip to facilitate penetration of the needle tip through tissue.

14. The device of claim 13, wherein the needle tip is separable from the elongate wire and is attached to the protective sheath, and extends distally from a distal end of the protective sheath.

15. The device of claim 14, wherein the needle tip is spaced apart from a distal end of the elongate wire when the protective sheath is in the distal position, and wherein the needle tip is in contact with the elongate wire when the protective sheath is in the proximal position to allow energy to be delivered from the elongate wire to the needle tip.

16. The device of claim 15, wherein the protective sheath is adapted to move from the distal position to the proximal position when the protective sheath is advanced into a tissue surface.

17. The device of claim 12, wherein the proximal abutment of the elongate shaft is configured to receive a force applied to the biasing element by movement of the protective sheath.

18. The device of claim 12, wherein the needle tip is formed on the distal end of the flexible elongate wire, and wherein the needle tip is positioned proximal to a distal-most end of the protective sheath when the protective sheath is in the distal position, and wherein the needle tip is exposed and extends from the protective sheath when the protective sheath is in the proximal position.

19. The device of claim 18, wherein the protective sheath is adapted to move from the distal position to the proximal position when the protective sheath is advanced into a tissue surface.

20. The device of claim 12, further comprising an expandable member disposed around a portion of the elongate shaft and adapted to expand radially relative to the elongate shaft.

21. The device of claim 20, wherein the expandable member comprises an expandable balloon.

22. The device of claim 12, wherein the needle tip is configured to form a puncture hole in tissue that has an extent that is substantially equal to a diameter of the protective sheath to allow the protective sheath to pass through the puncture hole.

* * * * *